United States Patent [19]

Holtkamp

[11] Plant 4,350

[45] Dec. 19, 1978

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Issellburg, Fed. Rep. of Germany

[21] Appl. No.: 880,054

[22] Filed: Feb. 22, 1978

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Beall & Jeffery

[57] ABSTRACT

An African violet known by the cultivar name Maine and characterized by large, single star-shaped flowers white in color, with violet-blue centers; strong, upright flower stems each carrying 4–5 flowers, and small, relatively light green foliage having serrated edges, with the flowers appearing just above the foliage crown.

5 Drawing Figures

The present invention comprises a new and distinct cultivar of African Violet plant, botanically known as *Saintpaulia ionantha,* hereinafter referred to by the cultivar name Maine. Maine, referred to in the breeding and selection process by the numbers b 288/4 and 82/77, is a product of a planned breeding program. Maine is generally characterized by its very large, star-shaped white flowers, with violet-blue centers, its short upright and erect flower stems, and the non-dropping characteristic of the flowers.

The new cultivar was originated from a cross made in a controlled breeding program in Isselburg, Rhineland, Germany. The female, or seed parent was an unpatented cultivar identified as BES I blue star (color RHS 89-B). The male, or pollen parent was also unpatented and identified as XVIII 148 white star.

Maine was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Maine, which in combination distinguish this African violet as a new and distinct cultivar.

1. Short, strong upright flower stems.
2. The flowers appear just above the crown of leaves.
3. 4–5 large single, star-shaped flowers on one flower stem.
4. White flower color, with a relatively small area near the center of the flower being violet-blue.
5. Occasionally, some flowers contain more than five petals.
6. Small, relatively light green leaves having serrated edges.

The accompanying photograph drawing shows a typical specimen plant of the new cultivar. The colors appearing in the photograph are as true as possible with color illustrations of this type.

In the description, color references are made to the Royal Horticultural Society color chart (RHS), 1966 edition, except where general color terms of ordinary significance are obvious.

Botanical classification: *Saintpaulia ionantha,* Ramat. cv Maine.

Parentage:

*Male parent.*—XVIII148 white star.

*Female parent.*—BES I blue star (color RHS 89-B).

Propagation: The new cultivar holds its distinguishing characteristics through successive propagations by leaf cuttings and by division of shoots.

Plant: From 7 cm. to 9 cm. tall when grown in pots, and approximately 22 cm. in diameter when fully grown.

*Leaves.*—General form: oblong. Diameter: 40–45 mm. Texture: very tender, slightly hairy. Aspect: borders are moderately to strongly serrated. Veins: very well pronounced. Color (upperside): relatively light green, 137 D. Color (underside): 149 D. Petiole: light green, slightly hairy.

*Flowers.*—Buds: round, diameter 8–9 m., color 145 D. Sepals: five; 7–8 mm. long, spear-shaped. Color: 144 B. Calyx: Flat, funnel-shaped. Aspect: Flowerstem and receptacle are connected. Penduncle: Slightly hairy, erect.

*Individual flowers.*—Size: The flower is up to 60 mm. in diameter, with individual petals being 23–25 mm. long and 22–23 mm. wide. Color: Upperside: 155D, middle of the flower, 92A. Underside: 155D. Borne: The flower stems carry up to five single flowers. Shape: Five petals of equal size, star-shape, with some flowers occasionally having more than five petals. Arrangement: Flowers are on strong, upright flower stems. Flowering time: 7–8 weeks after potting, the first flowers appear; after 9–11 weeks, the plant is in full bloom.

*Reproductive organs.*—Stamens: five in number. Anthers: 10 anthers, close together, color 7 A. Arrangement: The stamens have five short stems and are arranged around the seed-bud. Some petals are joined to the filament. Styles: color 87 A, 7–8 mm. long. Pollen color: 7C.

*Roots.*—The young plants have well-developed root systems; young root tips are white, turning brownish when older.

*Disease resistance.*—No disease problems noticed to date.

*General observations.*—Maine has very large flowers which are star-shaped and white in color, with violet-blue centers. Five petals of equal size are normally present, although some flowers have even more petals which are connected to the stems carrying the anthers. The flower buds are light green to yellowish white. The leaves are small and relatively light green. When blooming for the first time, the plant has 5–6 upright flower stems with 4–5 large single blossoms on short peduncles. The mature flowers do not drop.

I claim:

1. A new and distinct cultivar of African violet known by the cultivar name Maine and characterized by the combined characteristics of large, single star-shaped flowers white in color, with violet-blue centers; strong, upright flower stems each of which carries 4–5 flowers, and small, relatively light green foliage having serrated edges, with the flowers appearing just above the foliage crown.

* * * * *

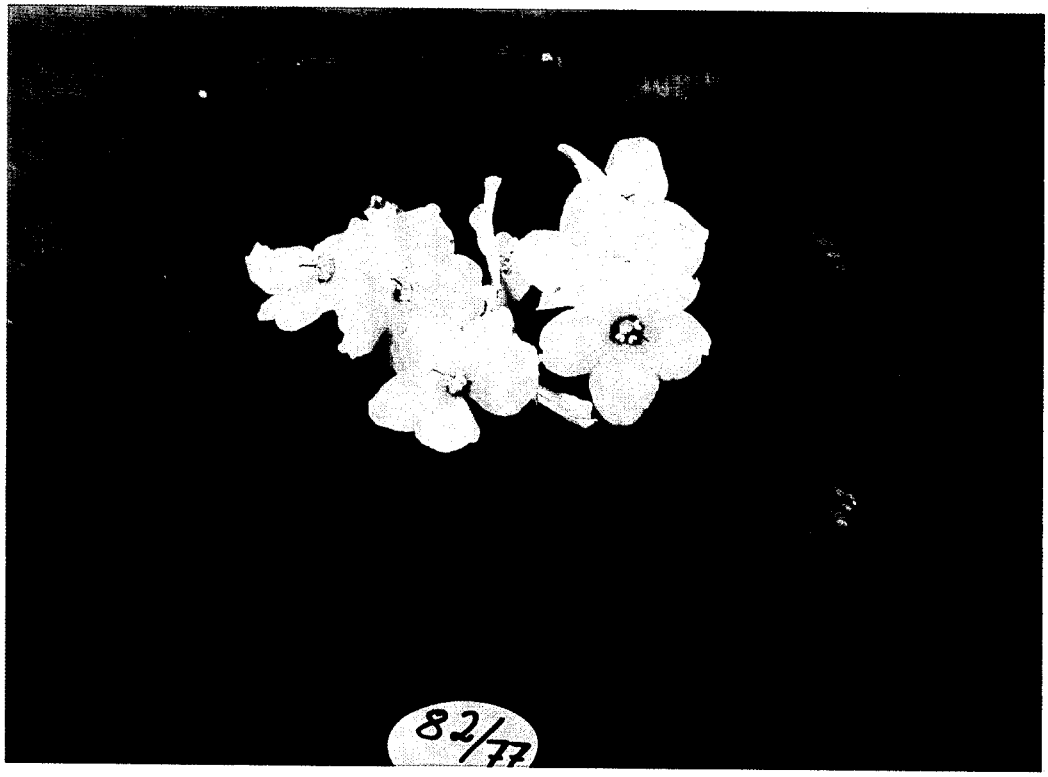
82/77